(12) United States Patent
Buechler et al.

(10) Patent No.: US 9,244,043 B2
(45) Date of Patent: Jan. 26, 2016

(54) INTEGRATED ACTIVE ULTRASONIC PROBE

(75) Inventors: Johannes Georg Rudolf Buechler, Siegburg (DE); York Oberdoerfer, Langenfeld (DE); Matthias Jobst, Dusseldorf (DE)

(73) Assignee: General Electric Company, Schenectady, NY (US)

( * ) Notice: Subject to any disclaimer, the term of this patent is extended or adjusted under 35 U.S.C. 154(b) by 601 days.

(21) Appl. No.: 13/592,930

(22) Filed: Aug. 23, 2012

(65) Prior Publication Data

US 2014/0056104 A1 Feb. 27, 2014

(51) Int. Cl.
*G01S 15/89* (2006.01)
*G01N 29/24* (2006.01)
*G01N 29/44* (2006.01)
*G01S 7/52* (2006.01)

(52) U.S. Cl.
CPC ............... *G01N 29/24* (2013.01); *G01N 29/44* (2013.01); *G01S 7/5208* (2013.01); *G01N 2291/106* (2013.01)

(58) Field of Classification Search
CPC . G01N 29/24; G01N 29/44; G01N 2291/106; G01S 7/5208
USPC .......................................................... 367/87
See application file for complete search history.

(56) References Cited

U.S. PATENT DOCUMENTS

| | | | |
|---|---|---|---|
| 6,491,634 B1* | 12/2002 | Leavitt et al. | 600/447 |
| 6,705,995 B1 | 3/2004 | Poland et al. | |
| 7,775,982 B2 | 8/2010 | Hazard et al. | |
| 2002/0120193 A1 | 8/2002 | Chiang et al. | |
| 2003/0097071 A1* | 5/2003 | Halmann et al. | 600/459 |
| 2004/0225220 A1 | 11/2004 | Rich | |
| 2007/0071266 A1 | 3/2007 | Little et al. | |
| 2014/0056104 A1* | 2/2014 | Buechler et al. | 367/87 |

FOREIGN PATENT DOCUMENTS

WO 2011163475 A1 12/2011

OTHER PUBLICATIONS

Search Report from PCT/US2013/050678 dated Nov. 5, 2013.
Triger S et al: "Low-voltage coded excitation utilizing a miniaturized integrated ultrasound system employing piezoelectric 2-D arrays", IEEE Transactions on Ultrasonics, Ferroelectrics and Frequency Control, IEEE, US, vol. 57. No. 2, Feb. 1, 2010, pp. 353-362.

* cited by examiner

*Primary Examiner* — Daniel Pihulic
(74) *Attorney, Agent, or Firm* — Barclay Damon, LLP

(57) ABSTRACT

An ultrasonic probe includes ultrasonic transducers and processing electronics to control emission of ultrasonic energy and to process and digitize returned echo data. Processed echo data can then be transmitted over a digital interface for display.

20 Claims, 2 Drawing Sheets

INTEGRATED ACTIVE ULTRASONIC PROBE

BACKGROUND OF THE INVENTION

The subject matter disclosed herein relates to ultrasonic probes, in particular, an integrated active ultrasonic probe that is connectable to a plurality of computing devices.

Nondestructive testing devices can be used to inspect, measure, or test objects to identify and analyze anomalies in the objects. These devices allow an inspection technician to maneuver a probe at or near the surface of the test object in order to perform testing of both the object surface and its underlying structure. Nondestructive testing can be particularly useful in some industries, e.g., aerospace, power generation, and oil and gas transport or refining (e.g., pipes and welds). The inspection of test objects must take place without removal of the object from surrounding structures, and where hidden anomalies can be located that would otherwise not be identifiable through visual inspection. Ultrasonic testing is one example of nondestructive testing. When conducting ultrasonic testing, ultrasonic pulses or beams are emitted from ultrasonic transducers mounted in a probe and pass through a test object. As the ultrasonic energy, in the form of pulses or beams, pass through the object, various ultrasonic reflections called echoes occur as the ultrasonic beams interact with internal structures (e.g., anomalies or surfaces) of the test object. These echoes are detected by the ultrasonic transducers and are analyzed by processing electronics connected to the ultrasonic transducers.

A phased array ultrasonic probe comprises a plurality of electrically and acoustically independent ultrasonic transducers that incorporate piezoelectric material and are mounted in a single probe housing. During operation, predetermined patterns of electrical pulses are generated and transmitted to the probe. The electrical pulses are applied to the electrodes of the phased array transducers causing a physical deflection in the piezoelectric material which generate ultrasonic energy (e.g., ultrasonic signals or beams) that is transmitted through the test object to which the probe is coupled. By varying the timing of the electrical pulses applied to the phased array ultrasonic transducers, the phased array ultrasonic probe generates ultrasonic beams that impact the test object at different angles. This process of beam steering facilitates an efficient inspection of different regions of the test object to completely detect anomalies therein. The amplitude and firing sequence of the individual transducers of the phased array probe can be programmably controlled in order to adjust the angle and penetration strength of the ultrasonic beam that is emitted into the test object. When the resulting ultrasonic echo returns to contact the surface of the piezoelectric material of a transducer it generates a detectable voltage difference across the transducer's electrodes which is then recorded as echo data by the processing electronics, and includes an amplitude and a delay time. By tracking the time difference between the transmission of the electrical pulses and the receipt of the echo data, and measuring the amplitude of the received echo data, various characteristics of the test object can be determined such as its thickness, or the depth and size of anomalies therein.

In some applications, the ultrasonic probe is connected to a dedicated processing station by cables which can be several meters long. The processing station drives the ultrasonic probe via the cables and the cables carry analog echo data detected by the transducers during a scanning inspection back to the processing station for analysis. The length of the cables tends to create added noise in the returning echo data. The processing station includes signal processing electronics for analyzing the echo data and a display screen for displaying the results of any analyses. The processing station hardware must match the type of the ultrasonic probe providing the echo data and is typically custom manufactured for each type of ultrasonic probe. For example, a probe having 128 transducers requires the same number of conductors in the cable to transmit echo data from each of the transducers in the probe head back to the processing station. For phased array ultrasonic probes containing such a large number of transducers, or more, the probe cable between the phased array probe and the processing station can be quite dense and is difficult to maneuver.

The discussion above is merely provided for general background information and is not intended to be used as an aid in determining the scope of the claimed subject matter.

BRIEF DESCRIPTION OF THE INVENTION

One aspect of the invention is an integrated active ultrasonic probe and a processing system operable with the integrated active ultrasonic probe. The integrated active ultrasonic probe includes specialized hardware and processing components required for generating ultrasonic test data which can be transmitted over a standard digital interface to a connected processing system. By moving specialized hardware and processing into the integrated active ultrasonic probe, the use of a generic processing system, or processing unit, such as a PC/workstation, laptop, or tablet, to analyze and visualize the ultrasonic echo data is facilitated. This relieves the requirement for specialized hardware and processing in the processing station. The new design is integrated into a small volume that fits into the probe housing that can be maneuvered within test objects. Signal-to-noise ratio is improved because shorter wires connect processing electronics directly to the ultrasonic transducers. The ultrasonic transducers and the processing of data generated thereby are part of the integrated active ultrasonic probe and heavy cables for housing significant data transmission lines are not required.

The ultrasonic probe includes ultrasonic transducers and processing electronics to control emission of ultrasonic energy and to process and digitize returned echo data. Processed echo data can then be transmitted over a standard digital interface. Advantages that may be realized in the practice of some disclosed embodiments of the integrated active ultrasonic probe is improved signal-to-noise and compatibility with various processing systems.

In one embodiment, an ultrasonic probe is disclosed comprising a plurality of ultrasonic transducers connected to an integrated circuit. The integrated circuit includes a plurality of transmitter and receiver circuits each generating electrical signals transmitted to one of the plurality of ultrasonic transducers and each receiving echo data detected by the one of the plurality of ultrasonic transducers. A control circuit is connected to the plurality of transmitter and receiver circuits to control the transmission of the electrical signals and to process the echo data. An analog-to-digital converter digitizes the processed echo data and a control unit receives the digitized and processed echo data for processing it into A-scan summation data. A digital interface is connected to the control unit for transmitting the A-scan summation data.

In another embodiment, a processing system for processing ultrasonic data is disclosed. The processing system includes a processing unit having a processor, a display, and a digital interface. An ultrasonic probe is connected to the digital interface and includes a number of ultrasonic transducers. An integrated circuit is connected to the plurality of ultrasonic transducers and includes a plurality of transmitter and receiver circuits. Each of the transmitter and receiver circuits generates electrical signals that are transmitted to one of the ultrasonic transducers and each receives echo data generated thereby. A control circuit is connected to the transmitter and receiver circuits to control the transmission of the electrical signals and to process the received echo data. An analog-to-digital converter is connected to the integrated circuit to digitize the processed echo data. A control unit is connected to the analog-to-digital converter to receive the digitized processed echo data and to process it into A-scan summation data. The A-scan summation data is then transmitted over the digital interface.

In another embodiment, a method of processing ultrasonic data is disclosed. The method includes receiving output data generated by an active integrated ultrasonic probe, which output data comprises beam formation data. A scan conversion of the beam formation data is performed and the beam formation data is decimated into a format compatible for display on a display screen. The scan converted beam formation data is combined into volume data and then rendered and displayed on the display screen.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
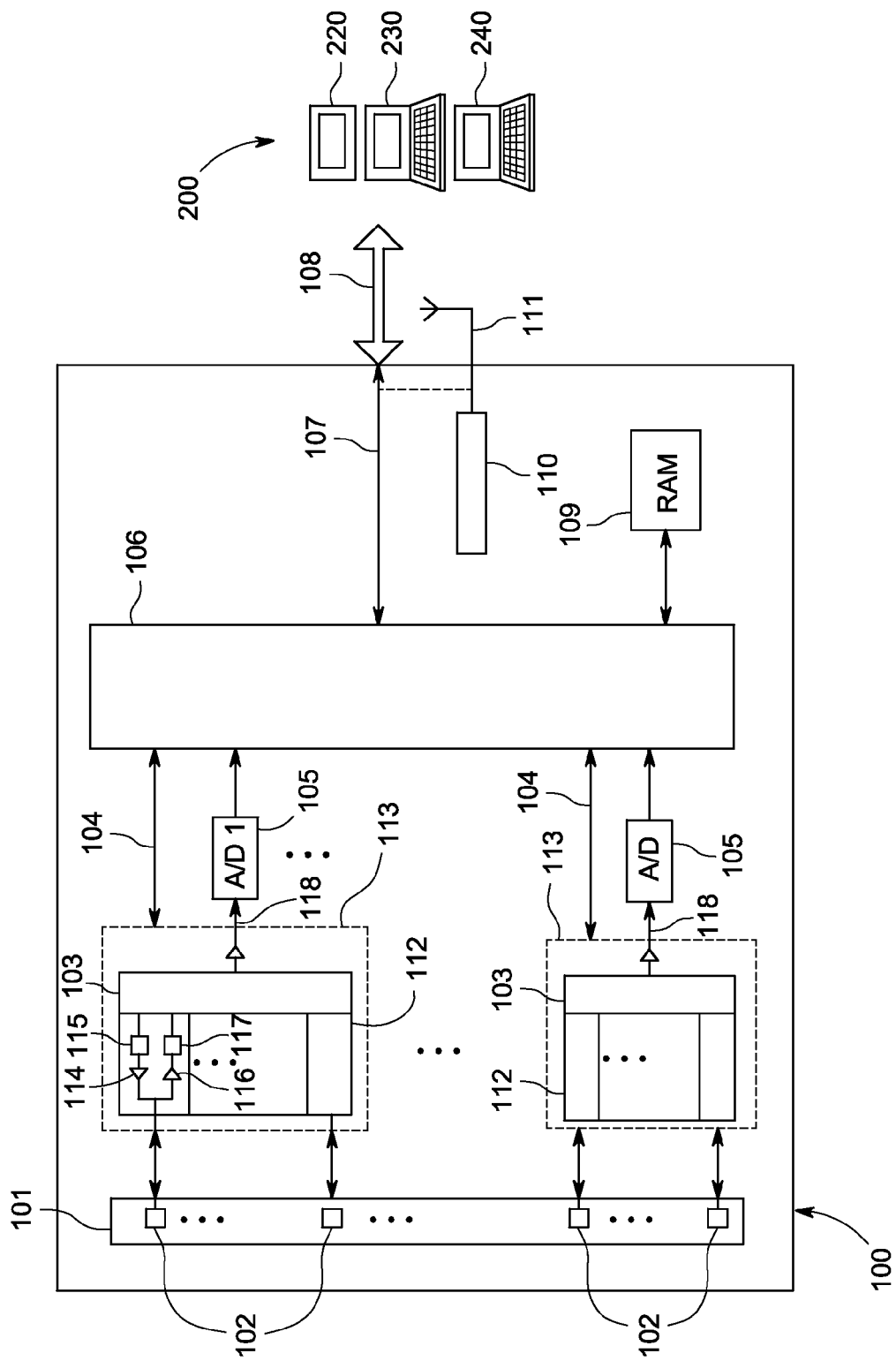
FIG. 1 is a schematic diagram of an exemplary phased array integrated active ultrasonic probe.

FIG. 1 illustrates an integrated active ultrasonic probe 100. In one embodiment, the integrated active ultrasonic probe 100 comprises an array 101 of ultrasonic transducers 102 each electrically connected to a transmitter and receiver circuit 112. The transmitter portion of the transmitter and receiver circuits 112 each comprise a pulser 114 that transmits electrical pulses to a connected one of the ultrasonic transducers 102. The pulsers 114 generate electrical pulses coordinated by control circuit 103 and buffered in transmitter delay circuits 115, including delays for controlling beam steering.

The receiver portion of the transmitter and receiver circuits 112 comprises an amplifier 116 and receiver delay 117 for receiving ultrasonic echoes detected by one of the connected ultrasonic transducers 102. In addition to controlling transmitter signals to the ultrasonic transducers 102, control circuit 103 sums the received echo data from all the transmitter and receiver circuits 112 connected to it, using receiver delay circuits 117, as part of a beam forming calculation process, and transmits the processed echo data to analog-to-digital (A/D) converter 105 over an application specific integrated circuit (ASIC) output port 118. Each ASIC 113 comprises an ASIC output port 118 connected to an A/D converter 105 for digitizing the ASIC output which can include A-scan data. A plurality of transmitter and receiver circuits 112, and a control circuit 103, can be fabricated on a single ASIC 113 having an ASIC output port 118. Thus, the beam formation is executed on the ASIC 113 which is disposed in the integrated active ultrasonic probe 100. By integrating the transmitter and receiver circuits 112 directly onto the ASIC 113 in the integrated active ultrasonic probe 100, the signal-to-noise ratios are improved due to the shorter electrical connection as compared to the conventional longer cable connections as described above.

A digital control unit 106, comprised of, for example, a field programmable gate array (FPGA), comprises an ASIC data interface 104 for communicating control data to the ASICs 113 and is connected to the A/D converters 105 for receiving the A/D converted data. The control unit 106 includes a digital interface 108 output. Such an interface can include, for example, a standard interface such as a USB interface, PCIe interface, WLAN interface, or Ethernet interface, to communicate with a connected generic processing unit 200 such as a tablet computer 220, a laptop computer 230, or a PC/workstation computer 240. The control unit 106 controls the different functions of the integrated active ultrasonic probe 100 and the ASICs 113. In one embodiment, four ASICs 113 are connected to the control unit 106, with each ASIC 113 typically connected to about thirty two ultrasonic transducers 102. This configuration of ultrasonic transducers 102 can be mounted within the integrated active ultrasonic probe 100.

The digital control unit 106 implements the standard digital interface 108 using digital transmission over a cable, e.g. USB, PCIe, Ethernet, or over a wireless interface, e.g., WLAN, for data transmission to the processing unit 200. The alternative wireless implementation uses battery 110 that provides power for wireless digital transmission via antenna 111. The data received from A/D converter 105 and processed by control unit 106 is typically clipped to 16 bit width before it is transmitted to the processing unit 200 over the standard digital interface 108.

The scheme for interrogating a test object is generated in probe control unit 106 and sent to the control circuit 103 in the form of a programmed beam steering operation. The interrogation scheme is stored, for example, in probe memory 109. The scheme might comprise, for example, a series of ultrasonic beams directed at the test object at particular angles wherein each beam in the series is slightly shifted by a predetermined number of degrees for a complete scan of the test object. Although the integrated active ultrasonic probe 100 is illustrated and described as a phased array probe, it should be noted that the integrated active ultrasonic probe 100 can include a single ultrasonic transducer 102, or a single ASIC 113 with multiple connected ultrasonic transducers 102.

Figure 2:
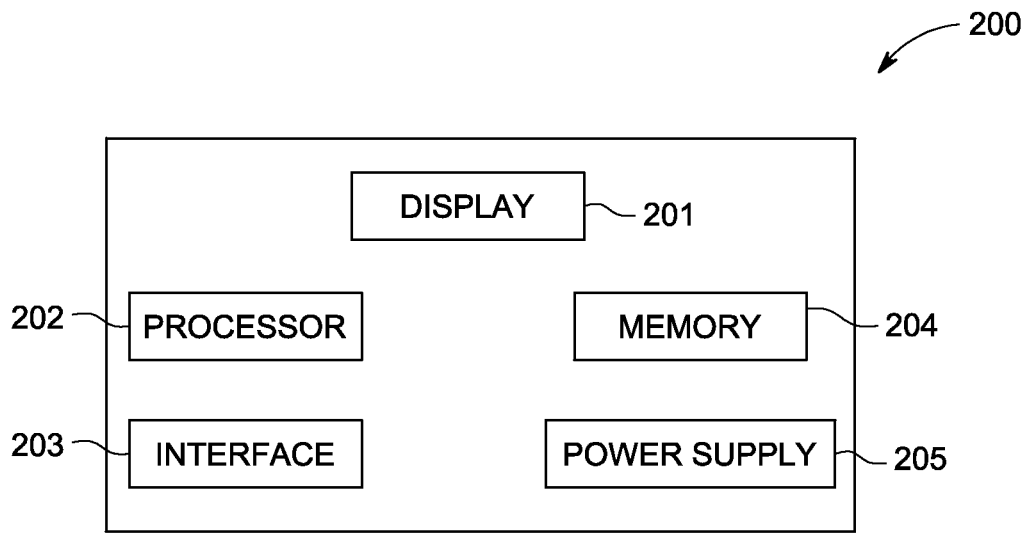
FIG. 2 is a diagram of an exemplary processing unit that is connected to the exemplary phased array integrated active ultrasonic probe of FIG. 1.

As shown in FIG. 2 the processing unit 200 can comprise any of several embodiments. The processing unit 200 can include a tablet computer 220, a laptop computer 230, or a PC/workstation computer 240. A peripheral digital interface 203, can connect the integrated active ultrasonic probe 100 to processing unit 200 for managing control and data communications between the processing unit 200 and the integrated active ultrasonic probe 100 or other components. The digital interface 203 can include, for example, a standard USB interface, Ethernet interface, or PCIe interface, or a wireless, e.g., WLAN or Bluetooth interface. Software installed on generic processing unit 200 enables controlled operation of integrated active ultrasonic probe 100 via a user interface. The software can be scaled in complexity to conform to the integrated active ultrasonic probe 100 hardware, for example, the number of transducers 102 mounted in the active ultrasonic probe 100. Control data sent from processing unit 200 to the integrated active ultrasonic probe 100 can include configuration set up, mode selection, and initialization data. Processing unit 200 includes one or more processor(s) 202, for running system software and controlling system operations, and processing unit memory 204 coupled to processor 202. Computer program instructions (executable instructions) can be stored in processing unit memory 204 or otherwise available to be executed by the processor 202 such as by downloading from a network. Processing unit 200 comprises a display screen 201 for a user to view system operations, user interface, and integrated active ultrasonic probe 100 inspection results. The processing unit 200 receives A-scan summation data generated by the control unit 106 of the integrated active ultrasonic probe 100. The received A-scan data are typically processed via scan conversion and decimation, after which they are displayed on an x-y graph with, for example, depth on the y-axis and distance from the transducer 102 on the x-axis, or with amplitude on the y-axis and time of flight on the x-axis. These displayed data form the signature of a potential anomaly and are typically stored in processing unit memory 204 and post processed to provide additional views for the operator to assist in determining if an anomaly is truly a defect or not. The processing unit 200 includes a power supply 205, connected to an external AC voltage or provided by a portable power source such as a battery.

Figure 3:
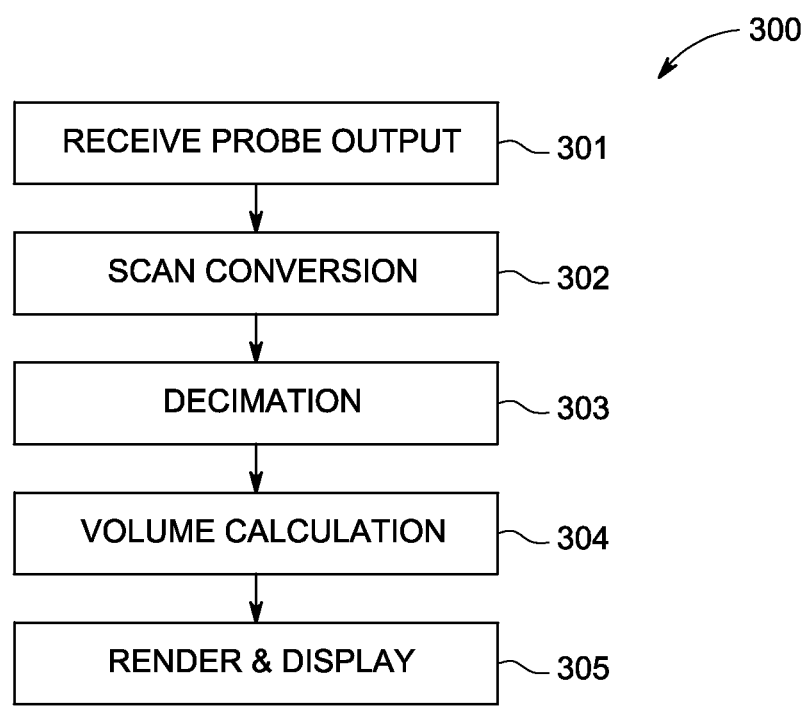
FIG. 3 is a flow diagram of an exemplary processing sequence performed by a generic processing unit connected to the integrated active ultrasonic probe of FIG. 1.

FIG. 3 illustrates a method 300 of processing data transmitted from the integrated active ultrasonic probe 100. After receiving the data output 301 from the integrated active ultrasonic probe 100, the first step in the processing unit 200 comprises a scan conversion 302 and a down sampling decimation step 303 for enabling the data to be displayed on display screen 201 of processing unit 200 with maximum resolution according to its display rate. Scan conversion 302 calculates an image from the beam formation data while decimation limits the sampling rate to about 1024 samples per beam. Afterwards the scan converted and decimated data is calculated and combined into a volume 304, which is then rendered and displayed 305 on display screen 201. The data transmission between the integrated active ultrasonic probe 100 and the processing unit 200 can implement a format where one data frame, i.e. one set of beams, is combined into one block for transmission to the processing unit 200. It should be noted that other methods of processing ultrasonic echo data output by the integrated active ultrasonic probe 100 can be implemented in the processing unit 200.

In view of the foregoing, embodiments of the invention combine an integrated active ultrasonic probe 100 with a compatible digital interface 108, e.g. a standard USB, PCIe, Ethernet, WLAN, or Bluetooth. A technical effect is improvement to the signal-to-noise ratio that is realized, as the transmitter and receiver for the ultrasonic signals is directly connected to the integrated active ultrasonic probe 100, at a distance of less than about 50 mm. It simplifies the connection between the integrated active ultrasonic probe 100 and the processing unit 200 due to bulky cables being replaced with standard digital interface 108 cables. With the standard digital interface 108 any commercially available processing unit 200 can be used with integrated active ultrasonic probe 100.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "circuitry," "unit," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasonic probe for emitting ultrasonic energy toward a test object and for receiving echo data generated thereby, the ultrasonic probe comprising:
   a plurality of ultrasonic transducers;
   an integrated circuit connected to the plurality of ultrasonic transducers, the integrated circuit comprising:
   a plurality of transmitter and receiver circuits, the plurality of transmitter and receiver circuits each generating electrical signals transmitted to one of the plurality of ultrasonic transducers for causing ultrasonic energy to be emitted therefrom, and each receiving the echo data detected by the one of the plurality of ultrasonic transducers; and
   a control circuit connected to the plurality of transmitter and receiver circuits for controlling the transmission of the electrical signals to the plurality of ultrasonic transducers and for processing the received echo data detected by the plurality of ultrasonic transducers to form processed echo data,
   wherein the plurality of transmitter and receiver circuits and the control circuit comprise a single integrated circuit and wherein the plurality of transmitter and receiver circuits are directly connected to the control circuit at a distance of less than 50 mm;
   an analog-to-digital converter connected to the integrated circuit for digitizing the processed echo data;
   a control unit connected to the analog-to-digital converter and receiving the digitized processed echo data for processing it into A-scan summation data; and
   a digital interface connected to the control unit for transmitting the A-scan summation data.

2. The ultrasonic probe of claim 1, wherein the plurality of transmitter and receiver circuits each comprise a pulser for generating the electrical signals transmitted to the one of the plurality of ultrasonic transducers and an amplifier for receiving the echo data detected by the one of the plurality of ultrasonic transducers.

3. The ultrasonic probe of claim 1, wherein the digital interface is connectable to a processing unit comprising a laptop computer, a tablet computer, a personal computer, or a combination thereof.

4. The ultrasonic probe of claim 1, wherein the digital interface is a wireless interface for transmitting the A-scan summation data wirelessly.

5. The ultrasonic probe of claim 4, wherein the digital interface comprises a Peripheral Component Interconnect Express interface, a Universal Serial Bus interface, an Ethernet interface, or a wireless local area network interface.

6. The ultrasonic probe of claim 1, wherein the received echo data comprises reflections of the ultrasonic energy emitted by the plurality of ultrasonic transducers impacting the one of the plurality of ultrasonic transducers.

7. The ultrasonic probe of claim 1, wherein the processed echo data comprises beam forming data.

8. The ultrasonic probe of claim 2, wherein the entire ultrasonic probe is contained within a single probe housing.

9. A processing system for processing ultrasonic data comprising:
   a processing unit comprising a processor, a display, and a digital interface; and
   an ultrasonic probe connected to the processing unit via the digital interface, the ultrasonic probe comprising:
   a plurality of ultrasonic transducers;
   an integrated circuit connected to the plurality of ultrasonic transducers, the integrated circuit comprising a plurality of transmitter and receiver circuits directly connected to the control circuit at a distance of less than 50 mm, the plurality of transmitter and receiver circuits each generating electrical signals transmitted to one of the plurality of ultrasonic transducers for causing emission of ultrasonic energy therefrom, and each receiving echo data detected by the one of the plurality of ultrasonic transducers, and a control circuit connected to the plurality of transmitter and receiver circuits for controlling the transmission of the electrical signals to the plurality of ultrasonic transducers and for processing the received echo data detected by the plurality of ultrasonic transducers, wherein the plurality of transmitter and receiver circuits and the control circuit comprise a single integrated circuit;
   an analog-to-digital converter connected to the integrated circuit for digitizing the processed echo data; and
   a control unit connected to the analog-to-digital converter and receiving the digitized processed echo data for processing it into A-scan summation data and transmitting the A-scan summation data over the digital interface.

10. The processing system of claim 9, wherein the display displays the A-scan summation data.

11. The processing system of claim 9, wherein the plurality of transmitter and receiver circuits each comprise a pulser for generating the electrical signals transmitted to the one of the plurality of ultrasonic transducers and an amplifier for receiving the echo data detected by the one of the plurality of ultrasonic transducers.

12. The processing system of claim 9, wherein the processing unit comprises a laptop computer, a tablet computer, or a workstation.

13. The processing system of claim 9, wherein the digital interface is a wireless interface for transmitting the A-scan summation data wirelessly.

14. The processing system of claim 13, wherein the digital interface comprises a Peripheral Component Interconnect Express interface, a Universal Serial Bus interface, an Ethernet interface, or a wireless local area network interface.

15. The processing system of claim 9, wherein the received echo data comprises reflections of the ultrasonic energy emitted by the plurality of ultrasonic transducers impacting the one of the plurality of ultrasonic transducers.

16. The processing system of claim 11, wherein the entire ultrasonic probe is contained within a single probe housing having a size that fits within a test object undergoing an ultrasonic inspection by the processing system.

17. The processing system of claim 9, wherein the processed echo data comprises beam forming data.

18. A method of processing ultrasonic data generated by an active integrated ultrasonic probe, the processed ultrasonic data to be displayed on a display screen, the method comprising:
    receiving output data from the active integrated ultrasonic probe, the integrated ultrasonic probe comprising an integrated circuit comprising a plurality of transmitter and receiver circuits directly connected to the control circuit at a distance of less than 50 mm and a control circuit, the output data comprising beam formation data;
    performing a scan conversion of the beam formation data and decimating the beam formation data into a format compatible with the display screen;
    combining the scan converted beam formation data into volume data; and
    rendering and displaying the volume data on the display screen.

19. The ultrasonic probe of claim 1, wherein the integrated circuit comprises an application specific integrated circuit (ASIC) and wherein the ultrasonic probe is integrated in the application specific integrated circuit.

20. The processing system of claim 9, wherein the integrated circuit comprises an application specific integrated circuit (ASIC).

* * * * *